(12) United States Patent
Landsberger (10) Patent No.: US 7,087,092 B1
(45) Date of Patent: Aug. 8, 2006

(54) ARTIFICIAL HAND FOR GRASPING AN OBJECT

(76) Inventor: Samuel L Landsberger, 6922 Lofty Grove Dr., Rancho Palos Verdes, CA (US) 90275

( * ) Notice: Subject to any disclaimer, the term of this patent is extended or adjusted under 35 U.S.C. 154(b) by 0 days.

(21) Appl. No.: 11/040,960

(22) Filed: Jan. 21, 2005

Related U.S. Application Data

(63) Continuation-in-part of application No. 10/237,511, filed on Sep. 9, 2002, now abandoned.

(51) Int. Cl.
*A61F 2/66* (2006.01)
(52) U.S. Cl. .......................... 623/57; 623/64; 294/99.1
(58) Field of Classification Search ............ 623/57–64; 294/86.31, 86.27, 99.1, 111
See application file for complete search history.

(56) References Cited

U.S. PATENT DOCUMENTS

| 1,725,588 | A | 8/1929 | Kosek |
| 2,364,313 | A | 12/1944 | Pecorella |
| 3,173,151 | A | 3/1965 | Glabiszewski |
| 3,538,515 | A | 11/1970 | Brown |
| 3,604,017 | A | 9/1971 | Brown et al. |
| 4,094,016 | A | 6/1978 | Eroyan |
| 4,114,464 | A | 9/1978 | Schubert et al. |
| 4,149,278 | A | 4/1979 | Frosch et al. |
| 4,159,545 | A | 7/1979 | Manning et al. |
| 4,167,044 | A | 9/1979 | Girard |
| 4,225,983 | A | 10/1980 | Radocy et al. |
| 4,246,661 | A | 1/1981 | Pinson |
| 4,332,038 | A | 6/1982 | Freeland |
| 4,595,333 | A | 6/1986 | Ono et al. |
| 4,623,354 | A | 11/1986 | Childress et al. |
| 4,650,492 | A | 3/1987 | Barkhordar |
| 4,661,187 | A | 4/1987 | Beasley |
| 4,685,924 | A | 8/1987 | Massey |
| 4,685,929 | A | 8/1987 | Monestier |
| 4,792,338 | A | 12/1988 | Rennerfelt |
| 4,865,613 | A | 9/1989 | Rizzo |
| 4,955,918 | A | 9/1990 | Lee |
| 4,990,162 | A | 2/1991 | LeBlanc et al. |
| 5,013,326 | A | 5/1991 | Horvath |
| 5,052,736 | A | 10/1991 | Loncaric et al. |
| 5,062,855 | A | 11/1991 | Rincoe |
| 5,080,682 | A | 1/1992 | Schectman |
| 5,085,665 | A | 2/1992 | Radocy et al. |
| 5,116,386 | A | 5/1992 | Scribner |
| 5,200,679 | A | 4/1993 | Graham |
| 5,219,366 | A | 6/1993 | Scribner |
| 5,222,986 | A | 6/1993 | Wright |
| 5,378,033 | A | 1/1995 | Guo et al. |
| 5,800,572 | A | 9/1998 | Loveall |
| 5,888,235 | A | 3/1999 | Jacobsen et al. |
| 5,888,246 | A | 3/1999 | Gow |

*Primary Examiner*—Bruce E Snow
(74) *Attorney, Agent, or Firm*—Charles H. Thomas (57) ABSTRACT

An artificial hand includes a finger group which is pivotally connected to a thumb. The finger group and thumb are resiliently biased toward one another. The finger group and thumb have hooked articulated distal ends. When the artificial hand and the object are brought together, the finger-group and the thumb part to allow the object to pass into a capture zone. The articulated distal ends bend inwardly to assist in the passage of the object. Once in the capture zone the finger group and thumb close about the object thereby holding it is place. The hooked distal ends also serve to retain the object within the capture zone. In another aspect of the invention the finger group includes two finger sub-groups which are also resiliently biased together to hold objects.

7 Claims, 9 Drawing Sheets

Fig_1

Fig_2

Fig-3

Fig_4

Fig_5

ARTIFICIAL HAND FOR GRASPING AN OBJECT

The present application is a continuation in part of U.S. application Ser. No. 10/237,511 filed Sep. 9, 2002, now abandoned.

BACKGROUND OF THE INVENTION

1. Field of the Invention

The present invention pertains generally to the field of prosthetics, and more particularly, to a method and associated apparatus for using an artificial hand to hold objects.

2. Description of the Prior Art

Artificial hands are well know in the art, and are utilized as a substitute for a hand which has been lost through amputation or birth defect. Some artificial hands employ a push button(s) to open and close the hand, consequently requiring additional steps which interrupt the natural use pattern of handling an object. Other artificial hands are operated through a cable or motors which can be controlled by muscular contractions of other parts of the user's body.

SUMMARY OF THE INVENTION

The present invention is directed to a method and associated apparatus for using an artificial hand to grasp an object. The operative principle of this invention is that it provides a device (called Easy-Feed) to receive and securely grasp an object in a manner that is as natural as possible; namely, one simply pushes the object directly against the dorsal (outer) surface of the fingertips to cause the hand to open and receive the object. The invention employs finger groups which easily move apart as the object and fingers are brought together in a natural manner. Once the object resides in the capture zone, the finger groups resiliently close about the object to retain it in position. A useful feature of the invention is that the force required to insert an object is usually less than the force required to release the object. We use the terms "self-energizing" and "natural" because the user simply pushes the object directly through the fingers into te secure grasp of te hand. No extra cognitive or physiological burden is placed upon the user to manipulate a cable and harness, activate myoelectric signals, or actuate auxiliary buttons in order to operate the hand.

In accordance with a preferred embodiment of the invention, an artificial hand for grasping an object comprises a first finger group movably connected to a second finger group wherein the first and second finger groups are resiliently biased toward one another. The finger groups have mutually facing volar surfaces and opposite dorsal surfaces. The volar surfaces of the first and second finger groups define a capture zone within which objects are held. When an object is pushed against the dorsal surfaces at the finger group ends, the first and second finger groups, upon contacting the object, spread away from each other, thereby accepting the object and allowing the object to pass into the capture zone. Once the object resides in the capture zone, the first and second finger groups resiliently close around the object to retain the object in place within the capture zone.

According to the invention, the first finger group includes a plurality of fingers (two in a preferred embodiment), and the second finger group includes a thumb. The plurality of fingers and the thumb residing in opposing relationship wherein the volar surfaces of the plurality of fingers and the thumb are curved toward one another to form the capture zone. The plurality of fingers and the thumb cooperate to form an object handling mechanism wherein, when an object is pushed against the dorsal surfaces at the tips of the finger groups with a first force, the plurality of fingers and the thumb spread away from each other allowing the object to pass into the capture zone. After the object passes into the capture zone, the plurality of fingers and the thumb resiliently close around the object in a grasping action.

When the artificial hand and the object are pulled apart with a second force, the plurality of fingers and the thumb spread away from each other thereby releasing the object. Due to the construction of the present invention, the second force is usually greater than the first force.

According to the invention, the plurality of fingers and the thumb each have a distal end. At least some of the distal ends are hook-shaped and articulated. That is, the distal ends are hooked or curved inwardly toward the capture zone. The hooked shaped helps retain the object within the capture zone, and the articulated distal ends bend inwardly to accept the object. Mechanical stops prevent the articulated distal ends from bending outwardly beyond a maximum limit.

In one broad aspect the present invention may be considered to be an artificial hand for grasping an object comprising a base and first and second finger groups movably joined to the base. Each of the finger groups has volar and dorsal surfaces, and a distal end. The finger groups are resiliently biased toward each other and define a capture zone between the Volar surfaces thereof. The finger groups are movable relative to each other between open and closed positions. In the closed position the finger groups define a plane of object entry between the distal ends of the finger groups. This plane of object entry extends through the capture zone and intersects the base. When the object is pushed along the plane of object entry against the dorsal surfaces of the distal ends of the finger groups, the distal ends of the first and second finger groups then spread apart from each other, thereby accepting the object and allowing the object to pass between the volar surfaces of the first and second finger groups and enter the capture zone. When this occurs the first and second finger groups resiliently close around the object to retain it within the capture zone.

In another broad aspect the invention may be considered to be an artificial hand comprised of a base and a pair of opposing finger groups connected to the base. Both of the finger groups have dorsal and volar surfaces and distal ends. At least one of the finger groups is a movable finger group with an instantaneous axis of rotation relative to the base so that the finger groups form a capture zone therebetween and are movable relative to each other between open and closed positions. In the closed positions the finger groups define a plane of object entry extending between the distal ends of the finger groups, through the capture zone and intersecting the base. The instantaneous axis of rotation for the movable finger group lies on the opposite side of the plane of object entry from the distal end of the movable finger group, when the finger groups are in the closed position. As a result, when an object is pushed along the plane of object entry against the dorsal surfaces of the distal ends of the finger groups, the finger groups then spread apart from each other, thereby accepting the object and allowing the object to pass between the volar surfaces of the finger groups and enter the capture zone, whereupon the finger groups resiliently close around the object to retain it within the capture zone.

In accordance with another aspect of the invention the plurality of fingers are connected to the body at a first pivotal axis and the thumb is connected to the body at a second pivotal axis. The pivotal axes are arranged in a crossover configuration wherein the pivotal axes are positioned toward the opposite member. This design provides the easy opening feature of the present invention.

In accordance with another aspect of the invention, the first finger group includes a first finger subgroup and a second finger subgroup which are resiliently biased toward one another. A second object may be placed between the first finger subgroup and the second finger subgroup and retained in place. The closing action of the first and second finger subgroups operates substantially perpendicular to the closing action of the plurality of fingers and the thumb.

Other aspects of the present invention will become apparent from the following detailed description, taken in conjunction with the accompanying drawings, which illustrate, by way of example, the principles of the invention.

The invention may be described with greater clarity and particularity by reference to the accompanying drawings.

DESCRIPTION OF THE DRAWINGS

DESCRIPTION OF THE EMBODIMENT

Figure 1:
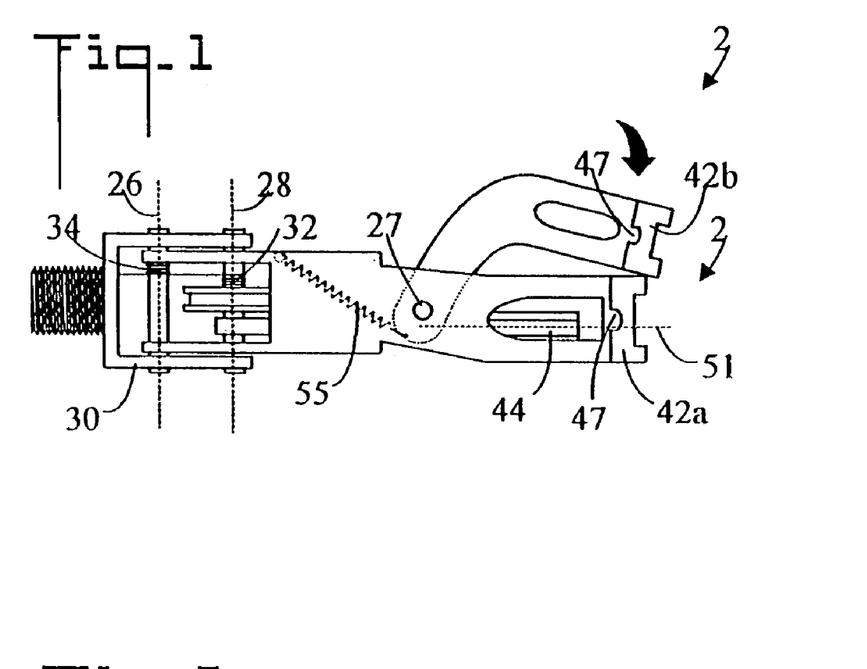
FIG. 1 is a top plan view of an artificial hand according to the present invention.
Figure 2:
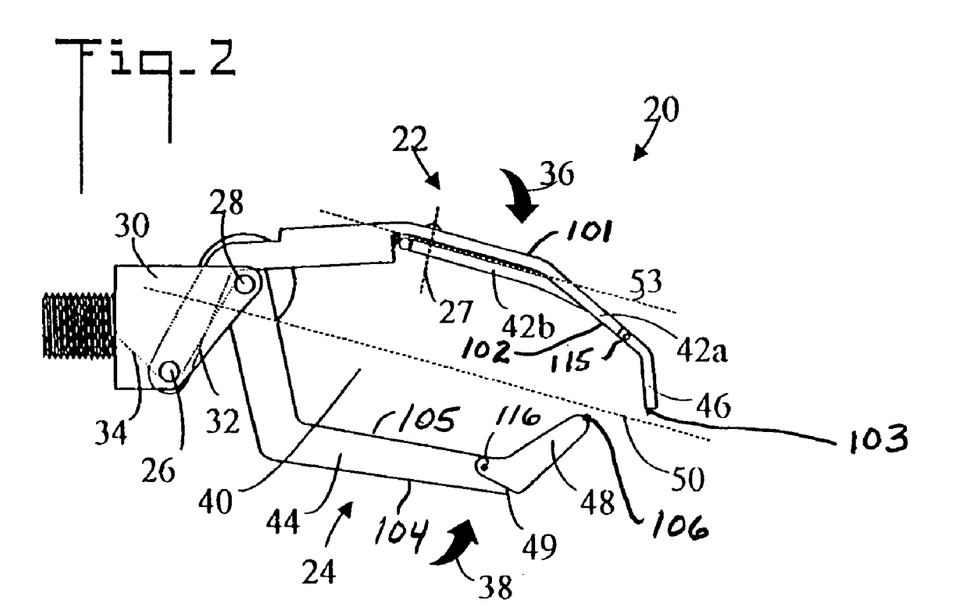
FIG. 2 is a side elevational view of the artificial hand of FIG. 1.
Figure 3:
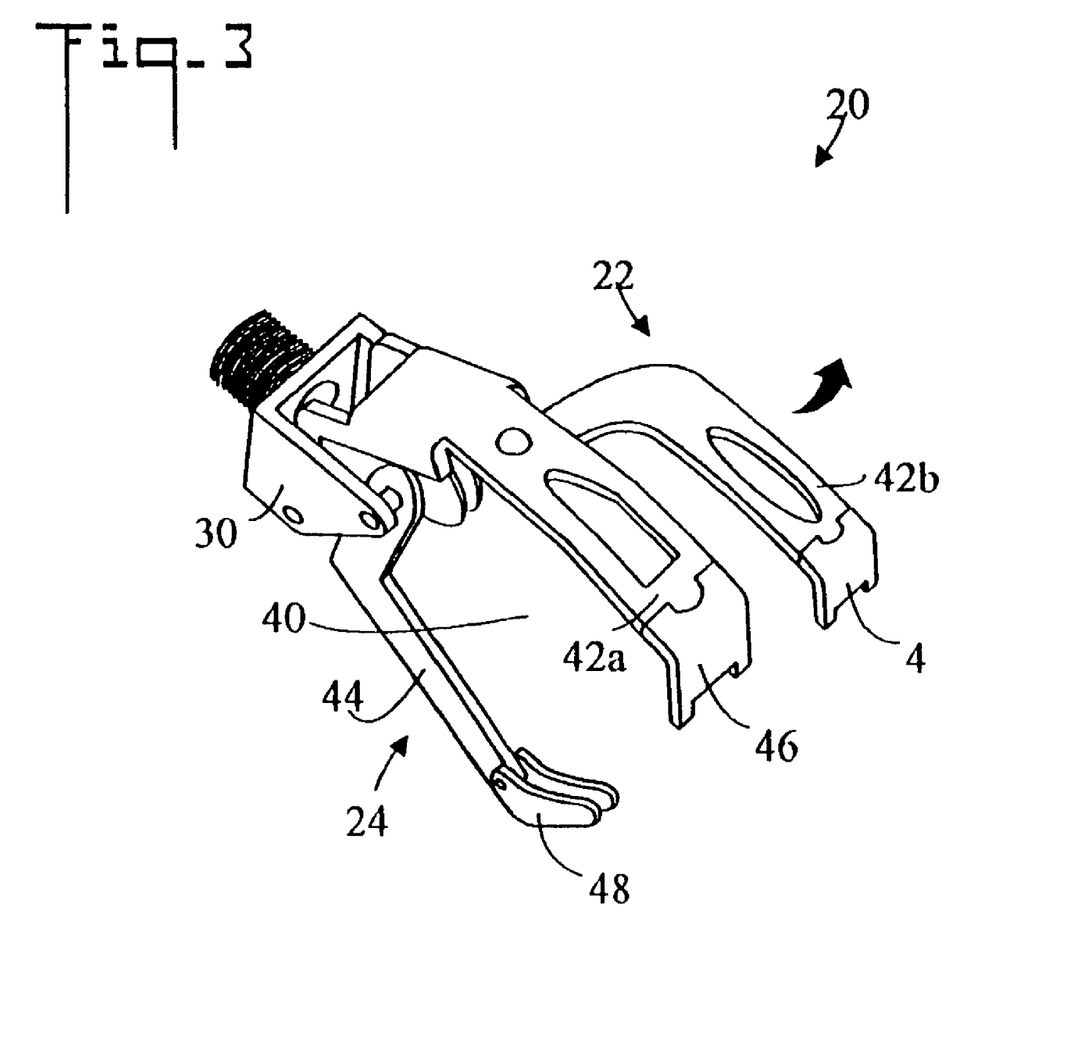
FIG. 3 is a perspective view of the artificial hand of FIG. 1.
Figure 4:
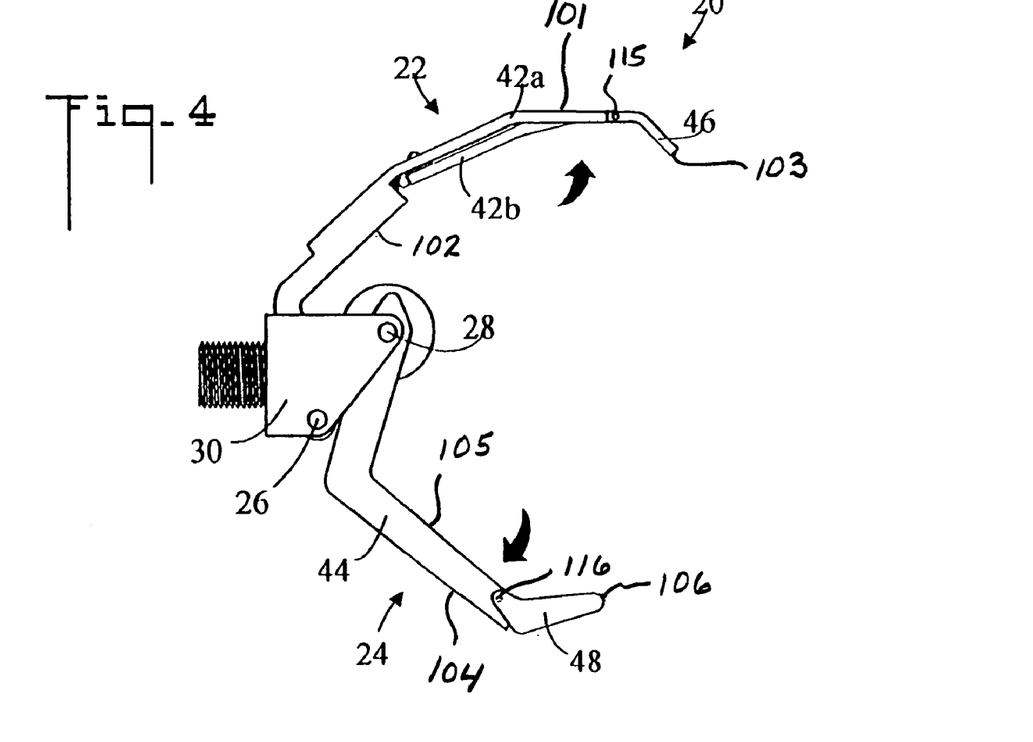
FIG. 4 is a side elevational view of the artificial hand of FIG. 1 illustrating the first finger group and the second finger group in an open position.

Referring initially to FIGS. 1–3, there are illustrated top plan, side elevational, and perspective views, respectively, of an artificial hand for grasping objects in accordance with the present invention, generally designated as 20. The artificial hand 20 includes a first finger group 22 movably connected to a second finger group 24 wherein the first finger group 22 and the second finger group 24 are resiliently biased toward one another as shown in FIG. 2. FIG. 4 shows the first finger group 22 and the second finger group 24 pivoted to an open position. The first finger group 22 pivots about a first pivotal axis (axle) 26, and the second finger group 24 pivots about a second pivot axis (axle) 28.

Figure 6:
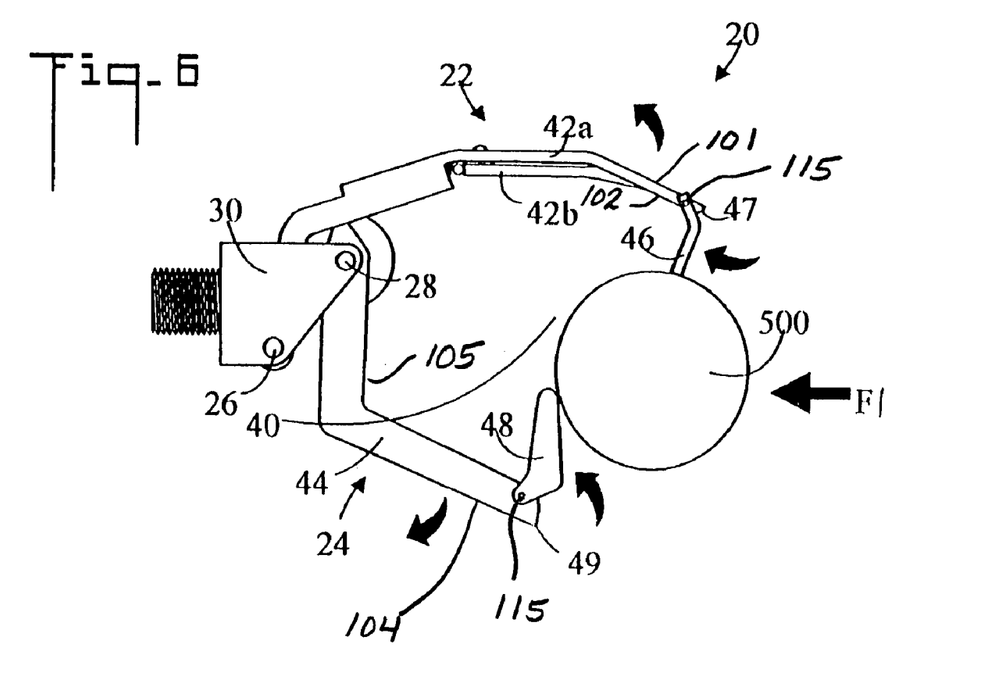
FIG. 6 is a side elevational view of the first finger group and second finger group being forced apart to capture an object.

The pivot axles 26 and 28 are connected to a body 30. The biasing effect is created by springs 32 and 34, which urge first finger group 22 in direction 36 and second finger group 24 in direction 38. First finger group 22 and second finger group 24 define a capture zone 40 therebetween. When the finger groups and an object 500 are pushed together, the first finger group 22 and second finger group 24 are rotated away from each other thereby accepting the object 500 and allowing the object 500 to pass between the first finger group 22 and second finger group 24 and enter capture zone 40, as shown in FIG. 6. Once the object 500 resides in capture zone 40, the first finger group 22 and second finger group 24 resiliently close around the object 500 to retain the object 500 within capture zone 40, as shown in FIG. 7.

In the embodiments of the invention illustrated, first finger group 22 includes a plurality of fingers (first finger subgroup 42a and second finger subgroup 42b). The second finger group 24 includes a thumb 44. The plurality of fingers 42a and 42b and thumb 44 reside in opposed relationship wherein the plurality of fingers 42a and 42b and thumb 44 are curved toward one another to form a capture zone 40 therebetween. In the embodiments illustrated, the first finger group includes two finger subgroups. However three or four finger subgroups could also be utilized.

Figure 7:
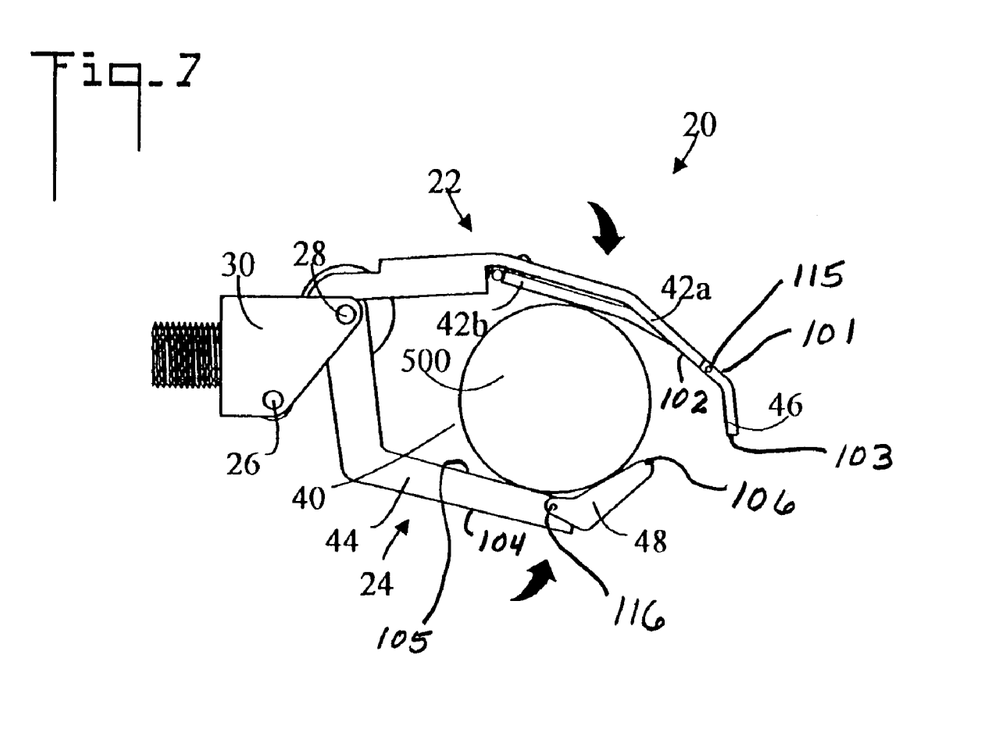
FIG. 7 is a side elevational view illustrating the object residing in the capture zone between the first and second finger groups.
Figure 8:
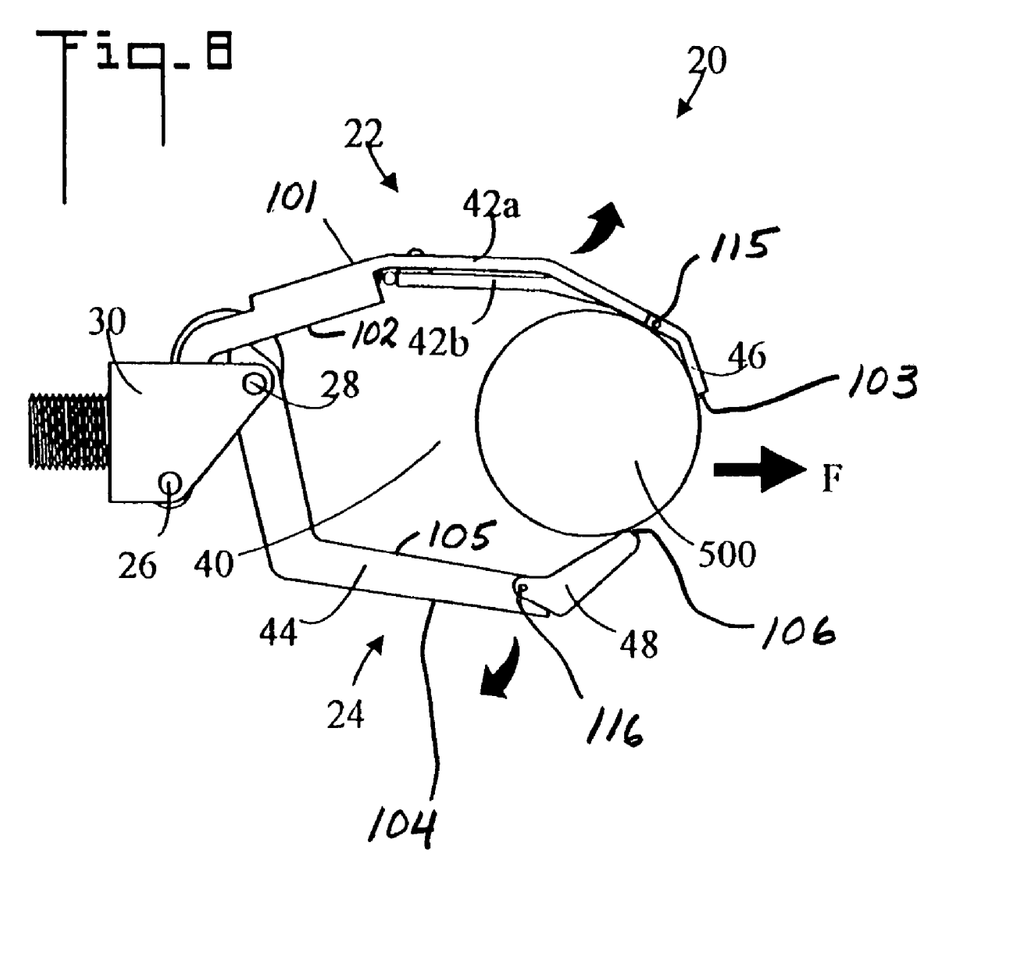
FIG. 8 is a side elevational view of the object being pulled out of the capture zone.

Now referring also to FIGS. 6–8, the plurality of fingers 42a and 42b and thumb 44 cooperate to form an object handling mechanism, wherein when the plurality of fingers 42a and 42b and thumb 44 and object 500 are pushed together with a first force FI, the plurality of fingers 42a and 42b and thumb 44 are forced apart and spread away from each other allowing object 500 to pass into capture zone 40. After passage, the plurality of fingers 42a and 42b and thumb 44 resiliently close around object 500. When artificial hand 20 and object 500 are pulled apart with a second force F2, plurality of fingers 42a and 42b and thumb 44 spread away from each other thereby releasing object 500. However, because of the construction of artificial hand 20, second force F2 is usually greater than first force F1. This is partially due to the "crossover" mounting arrangement of the finger groups 22 and 24 and partially due to the fact that the hooked ends of the plurality of fingers 42a and 42b and thumb 44 are curved or "hooked" toward each other as hereinafter described.

Both the first finger group 22 and the second finger group 24 may be considered to have both dorsal and volar portions or surfaces. Anatomically the dorsal portion of each finger group is the backside of the finger group opposite the palm of the hand up to and including the fingernail. The volar portion of the finger group is the side of the finger group facing the palm, up to but not including, the fingernail.

With reference to FIG. 2, the dorsal portion of the first finger group 22 is indicated at 101, while the volar portion of the first finger group 22 is indicated at 102. The demarcation or delineation between the dorsal and volar portions 101 and 102 of the first finger group 22 is at the point indicated at 103.

Likewise, the dorsal portion of the second finger group 24 is indicated at 104, while the volar portion of the second finger group 24 is indicated at 105. The demarcation or delineation between the dorsal portion 104 and volar portion 105 is at the point indicated at 106.

The elements of the invention may also be considered from a geometrical point-of-view, regarding the hand 20 as an object-grasping device with a capture zone 40 for holding objects, such as the object 500. An equivalent definition of the term "volar" is that the volar surfaces of the artificial hand 20 are the regions facing or bounding the capture zone 40. All other surfaces of the hand 20 may be considered to constitute dorsal surfaces.

By either definition the volar surfaces 102 and 105 of the finger groups 22 and 24, respectively, include the surfaces of the finger groups that face each other when the finger groups are closed together toward each other, as illustrated in FIG. 2. The pressing of an object against the dorsal surfaces 101 and 104 at the distal ends 46 and 48 of the finger groups 22 and 24, respectively, does not, therefore, include the wedging of an object between the finger groups so as to pry the apart, as this would involve pressing the object against the volar surfaces 102 and 105.

The relative movement of the first finger group 22 and second finger group 24 with respect to each other may be described in terms of relative movement about an "instantaneous axis of rotation". An "instantaneous axis of rotation" is a mechanical engineering term meaning the momentary center of axis of rotation of a body undergoing nonlinear motion in space. In the embodiments of the invention illustrated, the respective axes of rotation of the two finger groups 22 and 24 are located at 26 and 28, respectively, both of which are fixed relative to the body or base 30. However, in some embodiments of artificial hands according to the invention the axis of rotation of one or both finger groups is not necessarily stationary relative to the base, but sometimes shifts depending upon the relative positions of the finger groups with respect to each other. Consequently, the term "instantaneous axis" may more accurately describe the "crossover" feature of the finger groups, which is an important and unique feature of the present invention as contrasted with prior artificial hands.

That is, and as is evident in FIG. 2 of the application, the first finger group 22 and second finger group 24 (thumb) reside in opposed relationship with the digital ends 46 and 48 respectively thereof, curved or hooked toward one another to form the capture zone 40. As is evident in FIGS. 2, 6, and 7, a first straight line extending between the tip of the distal end 46 of the finger group 22 and the first pivot axis 26 intersects a second straight line extending between the tip of the distal end 48 of the thumb 24 and the second pivot axis 28. This "crossover" feature is shown in FIG. 111, which illustrates the artificial hand 20 with the finger groups in the same orientation as shown in FIG. 2, but with the first straight reference line extending between the tip 46 of the finger group 22 and the first pivot axis 26 labeled 107 and the second straight reference line extending between the tip of the distal end 48 of the second finger group (thumb) 24 and the second pivot axis 28 labeled as 108. The line 107 passes through demarcation 103 while the line 108 passes through demarcation 106. These lines 107 and 10.8 thereby "cross over" each other to define the "crossover" finger group arrangement unique to the artificial hand of the present invention.

Figure 12:
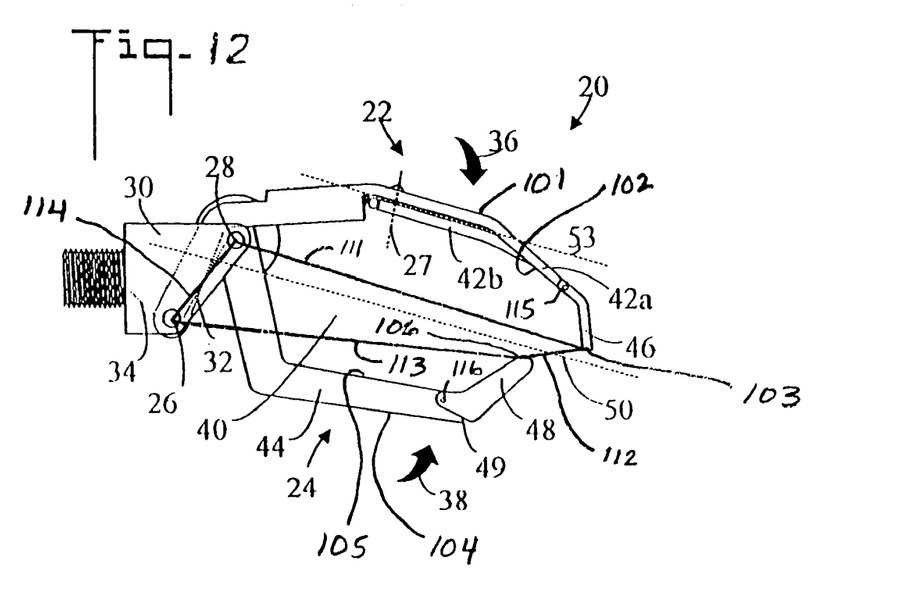
FIG. 12 is a side elevational view of the artificial hand of the invention as shown in FIG. 2 with different reference lines added to further illustrate the "crossover" finger group mounting arrangement of the invention.

This same "crossover" arrangement may be described in other geometric terms as well. For example, FIG. 12 is a diagram that shows the first and second finger groups 22 and 24 in the same relative positions as shown in FIG. 2. As illustrated in FIG. 12, the tip 46 of the distal end of the finger group 22, the second pivot axis 28, the first pivot axis 26, and the tip of the distal end 48 of the thumb 24 define the corners of a planar quadrilateral, the sides of which are labeled 111, 112, 113, and 114. As is evident from FIG. 12, the tip of the distal end 46 of the finger group 22 and the first pivot axis 26 are located at mutually opposite corners of the planar quadrilateral, while the tip of the distal end 48 of the second finger group (thumb) 24 and the second pivot axis 28 are located at the remaining corners of the quadrilateral, which are also mutually opposite each other.

Figure 5:
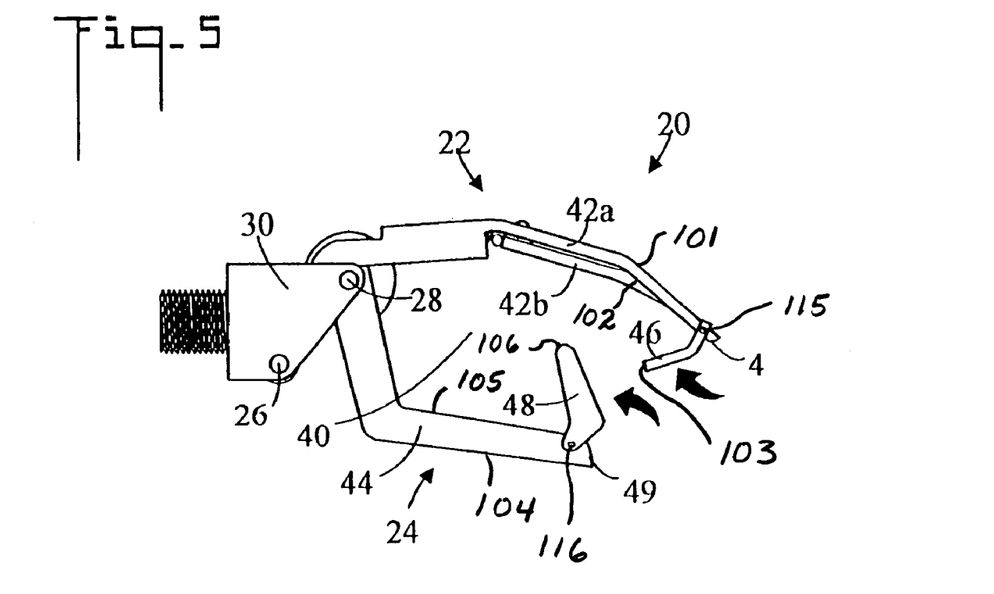
FIG. 5 is a side elevational view of the artificial hand of FIG. 1 illustrating the articulated distal ends of the first and second finger groups.

At least one of the plurality of fingers 42a and 42b has a distal end which is hooked (curved) inwardly toward capture zone 40. In the embodiments illustrated the distal end 46 of the first finger group 22 is hooked. Thumb 44 has a distal end 48 which is also hooked inwardly toward capture zone 40. In the embodiments of the invention illustrated, at least one of distal end 46 and distal end 48, and preferably both, are articulated so that when the plurality of fingers 42a and 42b and thumb 44 and the object 500 are pushed together, distal ends 46 and 48 bend inwardly toward: capture zone 40 thereby allowing the object 500 to enter capture zone 40, as shown in FIGS. 5 and 6. Distal ends 46 and 48 are restricted in counterrotation so that they do not bend outwardly away from capture zone 40. This arrangement thereby serves to retain object 500 in capture zone 40 as shown in FIG. 8. Outward bending is prevented by stops 47 and 49 respectively on distal ends 46 and 48, which limit opposite counterrotational movement from the finger end movement indicated in FIG. 6.

As illustrated in FIG. 6, the distal end 46 of the first finger group 22 is articulated. Therefore, when the finger group 22 and the object 500 are pushed together and toward the first and second axes 26 and 28, the distal end 46 of the first finger group 22 flexes inwardly toward the capture zone 40. This allows the object 500 to enter the capture zone 40. Contact of the object 500 is with dorsal surface 101.

Likewise, the distal end 48 of the second finger group 24 is also articulated. Therefore, when object 500 is pressed against the dorsal surface 105 of the second finger group 24 and toward the first and second axes 26 and 28, as illustrated in FIG. 6, the distal end 48 of the second finger group 24 also flexes inwardly towards the capture zone 40. The flexure of either or both of the distal ends 46 and/or 48 of the finger groups 22 and 24, respectively, thereby allows the object 500 to enter the capture zone 40.

Once the object 500 has entered the capture zone 40, as illustrated in FIG. 7, any force at all tending to withdraw the object 500 out of the capture zone 40 from between the distal ends 46 and 48 of the first and second groups 22 and 24, will cause the articulated distal ends 46 and 48 to counterrotate away from the axes 26 and 28 about their respective axes of rotation 115 and 116. Since there are limit stops 47 and 49 that limit the extent of counterrotation of the distal ends 46 and 48, the distal ends 46 and 48 can counterrotate to only a limited extent.

Furthermore, a light withdrawal force opposite the direction of force F1 and smaller in magnitude than force F1 tends to cause the finger groups 22 and 24 to rotate toward each other due to the "crossover" finger group mounting arrangement previously described. Therefore, the finger groups 22 and 24 cannot counterrotate enough to permit withdrawal of any but the tiniest objects 500. Consequently, withdrawal of an object 500, as illustrated in FIG. 8, will usually require a force F2 greater than the force F1 necessary to insert the object 500 into the capture zone 40.

A key aspect of the articulating distal finger ends 46 and 48 is that flexing the distal interphalangeal joints at the axes of rotation 115 and 116 in concert with the carpal joints at the axes 26 and 28 facilitates a "self-energizing" action of the hand. That is, as the object 500 is pushed against the dorsal surfaces of the distal finger ends 46 and 48, the ends 46 and 48 tend to flex inwardly. The object 500, with continued application of the force F1 shown in FIG. 5, continues movement deeper into the capture zone 40 in the palm region. This gives rise to and enhances extension torque that opens the carpals, i.e., the finger groups 22 and 24 in rotation away from each other about their respective axes 26 and 28, and thereby opens the hand 20. This permits full entry of the object 500 into the capture zone 40 of the hand. The combined flexure of either or both of the distal ends 46 and/or 48, together with the relative movement between the first finger group 22 and second finger group 24 is a unique feature of the artificial hand 20.

The term "self-energizing" as employed herein, means that the force F1 applied to the dorsal surfaces of the fingertips 46 and 48, necessary to insert an object 500 into the capture zone 40, is less than the force F2 required to spread the finger groups 22 and 24 apart from each other sufficiently for the object 500 to be removed from the capture zone 40. In contrast, a system which requires cables or some other force transmission mechanism, coupled to the muscles of the arm of the user, would not be a "self-energizing" system.

Referring to FIG. 2, a plane of object entry 50, separates distal end 46 of said plurality of fingers 42a and 42b and distal end 48 of thumb 44. The object handling mechanism further includes body 30. The plane of object entry 50 extends between the distal ends 46 and 48 of the finger groups 22 and 24 and through the body 30 between the axes of finger group rotation 26 and 28. As previously noted the plurality of fingers 42a and 42b are pivotally connected to body 30 at first pivot axis 26, and thumb 44 is pivotally connected to body 30 at second pivot axis 28. First pivot axis 26 is disposed on an opposite side of the plane of object entry 50 from second pivot axis 28. Because of this crossover axis placement, the plurality of fingers 42a and 42b and thumb 44 easily spread apart to allow object 500 to enter capture zone 40, but resist spreading apart if the object 500 is pulled away from the capture zone 40.

Figure 11:
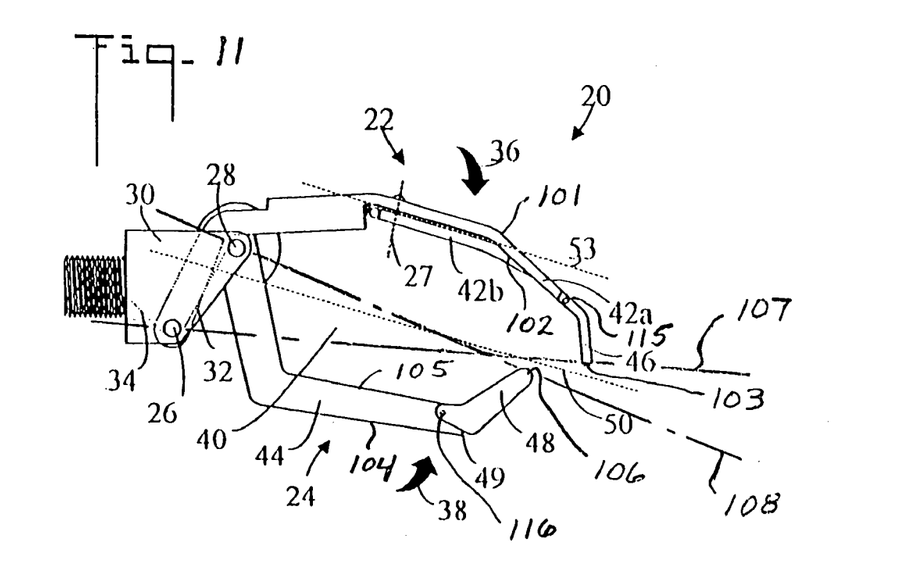
FIG. 11 is a side elevational view of the artificial hand as shown in FIG. 2 with reference lines added to illustrate the "crossover" finger group mounting arrangement of the invention.

As shown in FIG. 11, the "crossover" feature of finger group alignment means that the straight line 107 drawn between the extremity of the distal end 46 of the first finger group 22 and the axis of rotation 26 of the first finger group "crosses over" a second straight line 108 drawn between the extremity of the distal end 48 of the second finger group 24 and the axis of rotation 28 of the second finger group 24. According to this "crossover feature" the distal end 46 of the first finger group 22 and the first pivot axis 26 are located on opposite sides of the plane of object entry 50 from each other. Likewise, the distal end 48 of the second finger group 24 and the second pivot axis 28 are also located on opposite sides of the plane of object entry 50 from each other. Moreover, the distal end 48 of the second finger group 24 and the first pivot axis 26 are both located on the same side of plane of object entry 50. The distal end 46 of the first finger group 22 and the second pivot axis 28 are likewise both located on the same side of the plane of object entry 50.

Again referring to FIGS. 1 and 2, thumb 44 pivots in a thumb plane 51 (FIG. 1). Plurality of fingers 22 includes first finger subgroup 42a and second finger subgroup 42b. First finger subgroup 42a is pivotally connected to second finger subgroup 42b, wherein the first finger subgroup 42a and the second finger subgroup 42b are resiliently biased toward one another. Second finger subgroup 42b is pivotable about a third pivot axis 27 in a finger subgroup plane 53 (FIG. 2).

The third pivot axis 27 is substantially perpendicular to the thumb plane 51. When the first and second finger subgroups 42a and 42b and a second object 502 (such as a pencil) are pushed together, the first finger subgroup 42a and second finger subgroup 42b spread apart from each other thereby accepting the second object 502 and allowing the second object 502 to pass between first finger subgroup 42a and second finger subgroup 42b (refer also to FIGS. 9 and 10). Once the second object 502 resides between first finger subgroup 42 and second finger subgroup 42b, these finger subgroups resiliently close around the second object 502. The biasing action is provided by spring 55 which is connected between second finger subgroup 42b and body 30 (refer to FIG. 1).

FIG. 4 is a side elevation view showing plurality of fingers 42a and 42b and thumb 44 in an open position. Plurality of fingers 42a and 42b have pivoted about pivot first pivot axis 26, and thumb 44 has pivoted about second pivot axis 28.

FIG. 5 is a side elevation view showing the articulated distal end of the fingers 46 and thumb 48. Distal ends 46 and 48 bend (pivot) inwardly toward capture zone 40 and thereby accept object 500 (also refer to FIG. 6).

FIG. 6 is a side elevation view of an object 500 and the fingers 42a and 42b and thumb 44 being pushed together with a first force F1. It is noted that distal ends 46 and 48 pivot inwardly about their respective axes 115 and 116 to accept object 500. For those who have a sound hand, it is common practice to use the sound hand to place or push object 500 into contact with artificial hand 20 so that the object 500 enters capture zone 40.

FIG. 7 is a side elevation view of object 500 residing in capture zone 40 between fingers 42a and 42b and thumb 44.

FIG. 8 is a side elevation view of object 500 being pulled out of the capture zone 40 with a second force F2. Because distal ends 46 and 48 are hooked (curved), they tend to hold object 500 within capture zone 40. The force F1 required to push the object 500 into the capture zone 40 is therefore less than the force F2 required to withdraw the object 500 from the capture zone 40.

Figure 9:
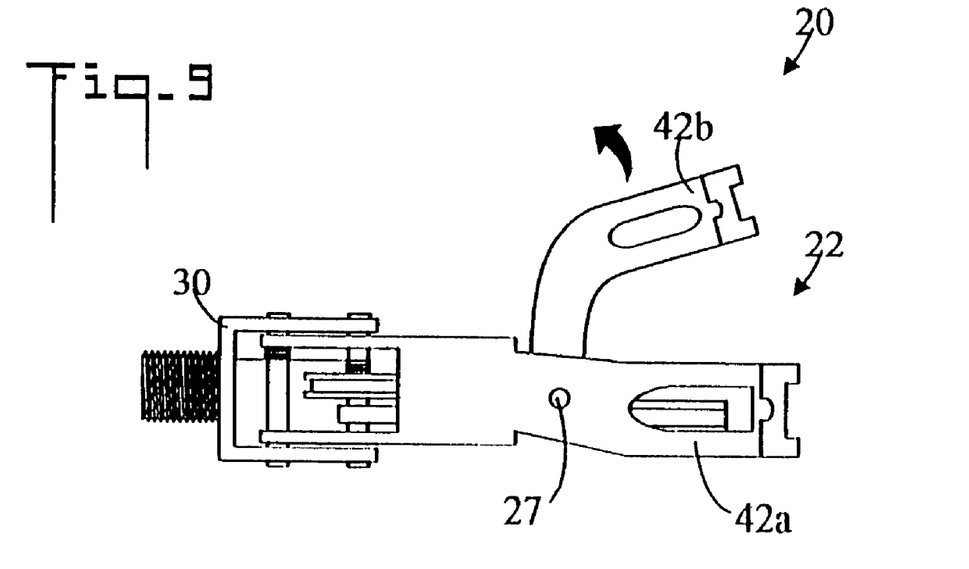
FIG. 9 is a top plan view illustrating a first finger subgroup and a second finger subgroup of the first finger group in an open position.

FIG. 9 is a top plan view of a first finger subgroup 42a and a second finger subgroup 42b in an open position. Second finger subgroup 42b has pivoted about third pivot axis 27.

Figure 10:
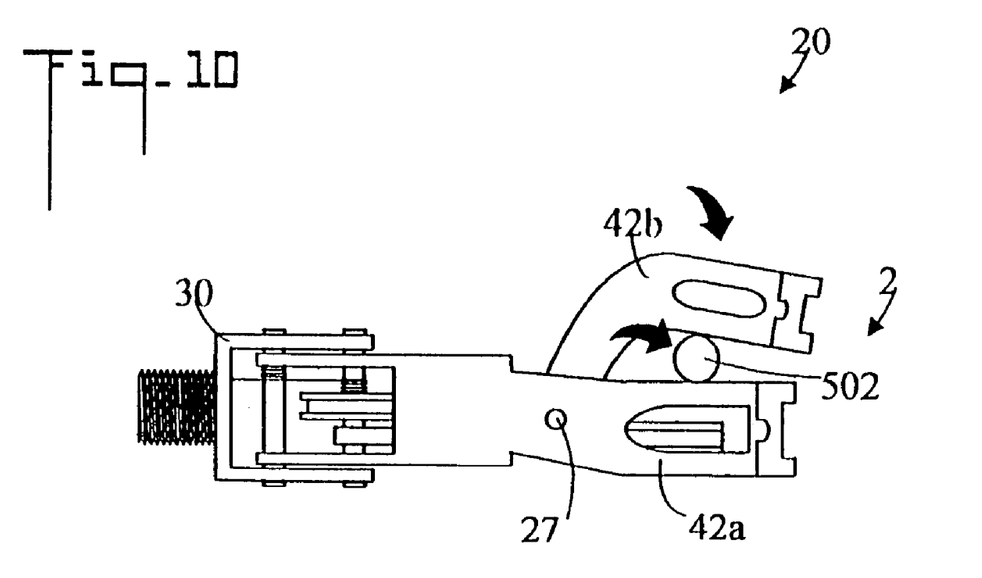
FIG. 10 is a top plan view illustrating the first finger subgroup and the second finger subgroup in a closed position with an object in the capture zone.

FIG. 10 is a top plan view of the first finger subgroup 42a and the second finger subgroup 42b closed around a second object 502; Second finger subgroup 42b has pivoted about third pivot axis 27 so that first 42a and second 42b finger subgroups close about object 502.

Figure 13:
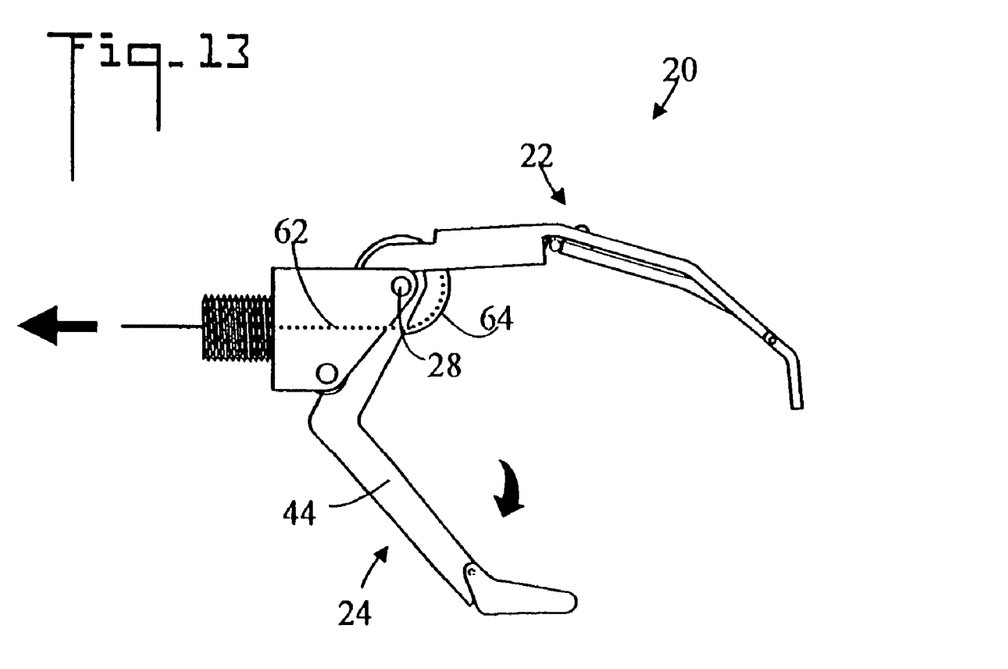
FIG. 13 is a side elevational view illustrating the second finger group (thumb) being opened by a cable.

FIG. 13 is a side elevation view showing thumb 44 being opened by a cable 62. Cable 62 is connected to pulley 64 which in turn is connected to thumb 44. When cable 62 is pulled it turns pulley 64 which causes thumb 44 to open.

Figure 14:
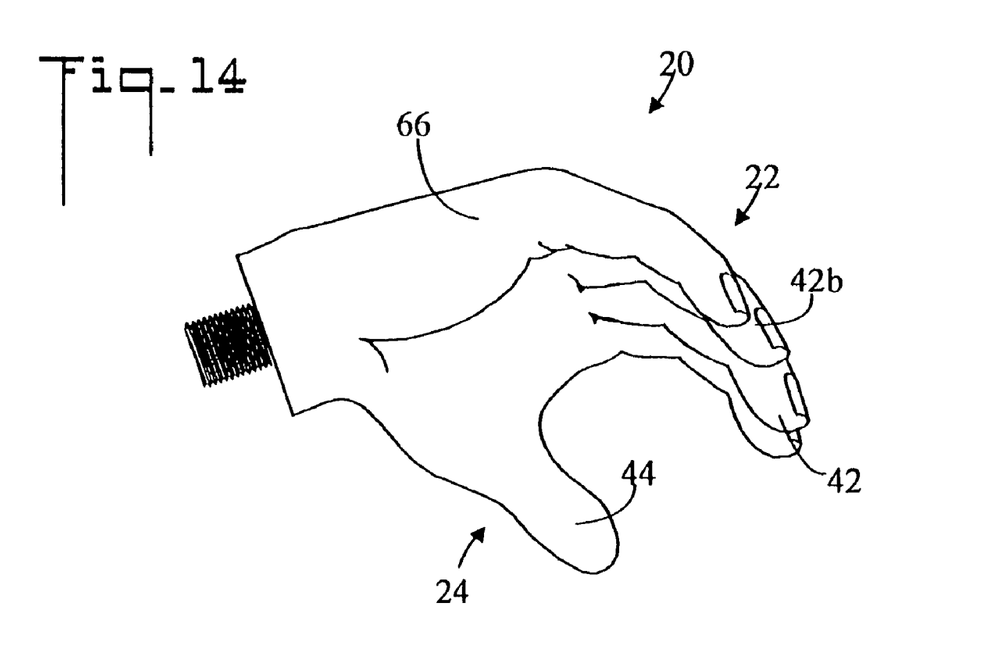
FIG. 14 is a perspective view of the artificial hand covered with a flexible material to produce a realistic appearance.

FIG. 14 is a perspective view of artificial hand 20 covered with a flexible material 66 to produce a realistic appearance.

Figure 15:
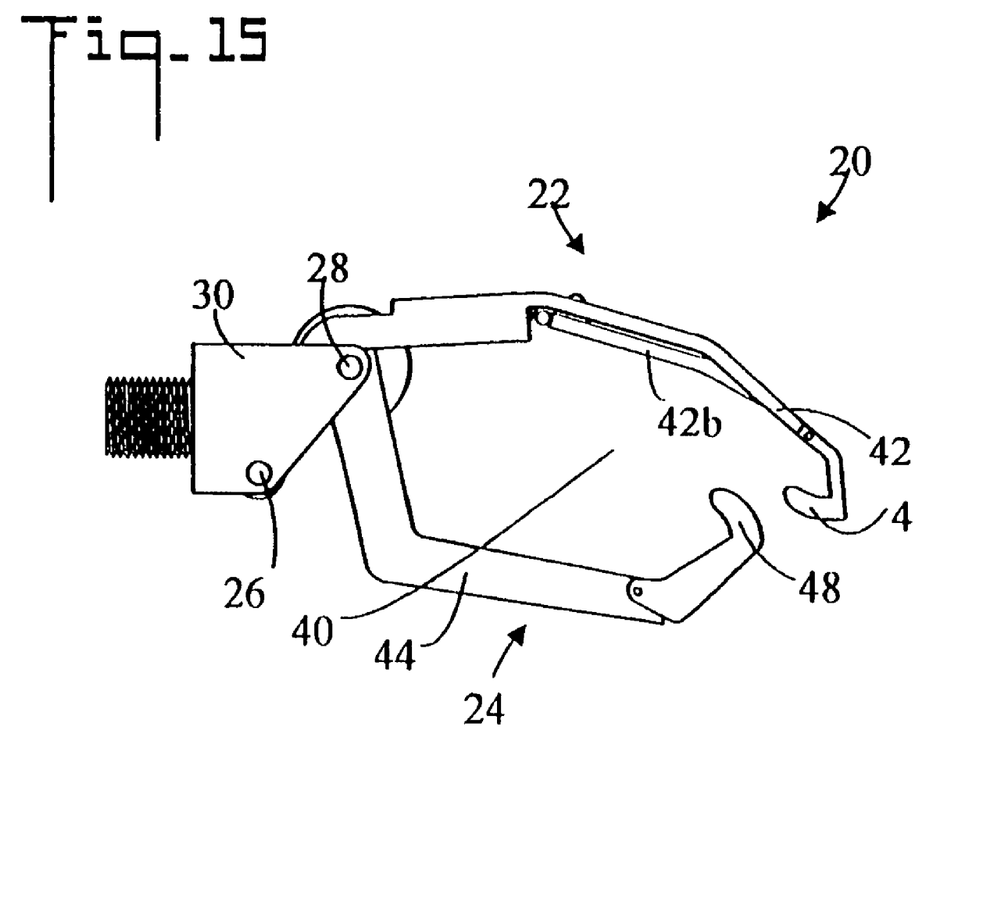
FIG. 15 is a side elevational view of a second embodiment of the hooked distal ends of the first finger group and the second finger group.

FIG. 15 is a side elevation of a second embodiment of the hooked distal ends 46 and 48 of the finger group 22 and thumb group 24 respectively. In this embodiment distal ends 46 and 48 are even more sharply hooked to better retain objects within capture zone 40.

In terms of use, a method of using an artificial hand 20 for grasping an object 500, comprises the steps of:

(a) providing an object 500;

(b) providing an artificial hand 20 for grasping the object 500, the artificial hand 20 comprising:

a first finger group 22 movably connected to a second finger group 24, wherein the first finger group 22 and second finger group 24 are resiliently biased toward one another;

the first finger group 22 and second finger group 24 defining a capture zone 40 therebetween;

(c) pushing the finger groups and the object 500 together into contact, wherein the first finger group 22 and second finger group 24 spread away from each other thereby accepting the object 500 and allowing the object 500 to pass between the first finger group 22 and second finger group 24 and enter the capture zone 40; and, (d) once the object 500 resides in the capture zone 40, the first finger group 22 and second finger group 24 resiliently closing around the object 500 to retain the object 500 within the capture zone 40.

The method further including:

in step (b), the first finger group 22 including a plurality of fingers 42a and 42b;

the second finger 24 including a thumb 44;

the plurality of fingers 42a and 42b and the thumb 44 residing in opposed relationship wherein the plurality of fingers 42a and 42b and the thumb 44 are curved toward one another to form capture zone 40;

in step (c), pushing the plurality of fingers 42a and 42b and the thumb 44 and the object 500 together with a first force F1; and, (e) pulling the artificial hand 20 and the object 500 apart with a second force F2, so that the plurality of fingers 42a and 42b and the thumb 44 spread away from each other thereby releasing the object 500, wherein the second force F2 is greater than the first force F1.

The method further including:

in step (b), each of the plurality of fingers 42a and 42b having a distal end 46 with at least one distal end 46 being hooked.

The method further including:

in step (b), the thumb 44 having a hooked distal end 48.

The method further including:

in step (b), each of the plurality of fingers 42a and 42b having a distal end 46 with at least one distal end 46 being hooked.

at least one distal end 46 being articulated; and, in step (c), when the plurality of fingers 46 and the object 500 are pushed together, the distal end 46 bending inwardly toward the capture zone 40 thereby allowing the object 500 to enter the capture zone 40.

The method further including:

in step (b), the distal end 46 not bending outwardly away from the capture zone 40 thereby retaining the object 500 in the capture zone 40 in step (d).

The method further including:

in step (b), thumb 44 having a distal end 48;

the distal end 48 being hooked;

the distal end 48 being articulated; and, in step (c), when thumb 44 and the object 500 are pushed together, the distal end 48 bending inwardly toward the capture zone 40 thereby allowing the object 500 to enter capture zone 40.

The method further including:

in step (b), the distal end 48 not bending outwardly away from capture zone 40 thereby retaining the object 500 in capture zone 40 in step (d).

The method further including:

in step (b), the plurality of fingers 42a and 42b having a distal end 46, and the thumb 44 having a distal end 48;

a plane of object entry 50 separating the distal end 46 of the plurality of fingers 42a and 42b and the distal end 48 of thumb 44;

artificial hand 20 having a body 30;

plurality of fingers 42a and 42b pivotally connected to body 30 at a first pivot axis 26;

thumb 44 pivotally connected to body 30 at a second pivot axis 28;

plurality of fingers 42a and 42b and thumb 44 resiliently pivotally biased toward one another; and the first pivot axis 26 disposed on an opposite side of the plane of object entry 50 from the second pivot axis 28; and, so that in step (c) because of the crossover placement of the first pivot axis 26 and second 28 pivot axis, the plurality of fingers 42a and 42b and the thumb 44 easily spread apart to allow the object 500 to enter capture zone 40.

The method further including:

providing a second object 502;

in step (b), the thumb 44 pivoting in a thumb plane 51, the plurality of fingers including a first finger subgroup 42a and a second finger subgroup 42b, the first finger subgroup 42a pivotally connected to the second finger subgroup 42b, wherein the first and second finger subgroups 42a and 42b are resiliently biased toward one another, the second finger subgroup 42b pivotable in a finger subgroup plane 53 which is substantially perpendicular to the thumb plane 51;

pushing the first and second finger subgroups 42a and 42b and the second object 502 together;

the first and second finger subgroups 42a and 42b spreading apart and accepting the second object 502 and allowing the second object 502 to pass between the first and second finger subgroups 42a and 42b; and once the second object 502 resides between the first and second finger subgroups, the first and second finger subgroups resiliently closing around the second object 502.

The preferred embodiments of the invention described herein are exemplary only, and numerous modifications, variations, and rearrangements can be readily envisioned to achieve an equivalent result, all of which are intended to be embraced within the scope of the appended claims. Undoubtedly, numerous variations and modifications of the invention will become readily apparent to those familiar with the construction and use of artificial hands. For example, a sensor (mechanical, electric, optical, or ultrasound) might be incorporated in the dorsal tips of the fingers to sense an object's presence, and thereby signal to a motor to open the hand to admit the object. Although addition of a sensor and a electric-mechanical activation unit would add to the complexity of the hand structure, note that it would nevertheless still provide natural, self-energizing action with minimal tasking of the user, and indeed, provide for even lower activation force and better grip, since auxiliary power is available. Accordingly, the scope of the invention should not be construed as limited to the specific embodiment depicted and described, but rather is defined in the claims appended hereto.

I claim:

1. An artificial hand for grasping an object comprising:
a base,
a first finger group movably joined to said base and having volar and dorsal surfaces and a distal end,
a second finger group joined to said base and having volar and dorsal surfaces and a distal end,
wherein said finger groups are resiliently biased toward each other and said finger groups define a capture zone between said volar surfaces thereof and are movable relative to each other between open and closed positions, and in said closed position define a plane of object entry between said distal ends of said finger groups, and said plane of object entry extends through said capture zone and intersects said base,
wherein when said object is pushed along said plane of object entry against said dorsal surfaces of said distal ends of said finger groups, said distal ends of said first and second finger groups then spread away from each other, thereby accepting said object and allowing said object to pass between said volar surfaces of said first and second finger groups and enter said capture zone, whereupon said first and second finger groups resiliently close around said object to retain it within said capture zone.

2. An artificial hand comprised of a base, and
a pair of opposing finger groups connected to said base, both of said finger groups having dorsal and volar surfaces and distal ends, wherein at least one of said finger groups is a movable finger group with an instantaneous axis of rotation relative to said base so that said finger groups form a capture zone therebetween and are movable relative to each other between open and closed positions, and in said closed position define a plane of object entry extending between said distal ends of said finger groups, through said capture zone and intersecting said base, and
wherein said instantaneous axis of rotation for said movable finger group lies on the opposite side of said plane of object entry from said distal end of said movable finger group, when said finger groups are in said closed position,
whereby when an object is pushed along said plane of object entry against said dorsal surfaces of said distal ends of said finger groups, said finger groups then spread away from each other, thereby accepting said object and allowing said object to pass between said volar surfaces of said finger groups and enter said capture zone, whereupon said finger groups resiliently close around said object to retain it within said capture zone.

3. An artificial hand according to claim 2, wherein said distal end of said movable finger group is hooked toward said capture zone.

4. An artificial hand for grasping an object, comprising:
a base;
a plurality of fingers having a distal end and movably connected to said base with a first instantaneous axis of rotation relative to said base;
a thumb having a distal end movably connected to said base with a second instantaneous axis of rotation relative to said base;
wherein said plurality of fingers and said thumb are curved toward one another to form a capture zone therebetween and are resiliently, movably biased toward one another to define a plane of object entry that separates said distal end of said plurality of fingers from said distal end of said thumb and passes through said capture zone and intersects said base, and when said finger groups are closed toward each other, said first instantaneous axis of rotation of said plurality of fingers is disposed on an opposite side of said plane of object entry from said distal end of said plurality of fingers, and said second instantaneous axis of said thumb is disposed on an opposite side of said plane of object entry from said distal end of said thumb;
whereby when said object is pushed against said distal end of said fingers and said distal end of said thumb toward said base along said plane of object entry with a first force, said plurality of fingers and said thumb spread apart allowing said object to pass into said capture zone, whereupon said plurality of fingers and said thumb resiliently close around said object constraining said object within said capture zone.

5. An artificial hand for grasping an object comprising:
a first finger group including a plurality of fingers;
a second finger group including a thumb;
wherein said first and second finger groups are curved toward one another in opposed relationship to define a capture zone therebetween; and said finger groups have distal ends that are resiliently biased toward one another, and at least one of said distal ends is articulated;
wherein when said object and said distal ends are pushed together with a first force said articulated distal end bends inwardly toward said capture zone and said first and second finger groups spread apart thereby allowing said object to pass into said capture zone; and
after said passage, said plurality of fingers and said thumb resiliently close about said object.

6. An artificial hand according to claim 5 further including:
a unidirectional stop on said articulated distal end so that said articulated distal end is limited in bending outwardly away from said capture zone, thereby retaining said object in said capture zone.

7. An artificial hand according to claim 6 further characterized in that:
said unidirectional stop restricts extension with a preset limit force such that a sufficiently strong withdrawal force will override said unidirectional stop and permit said object to leave said capture zone.

* * * * *